United States Patent [19]
Wilk

[11] Patent Number: 5,219,336
[45] Date of Patent: Jun. 15, 1993

[54] TAPE STRIP AND ASSOCIATED METHOD OF CONNECTING TUBULAR MEMBERS

[76] Inventor: Peter J. Wilk, 185 W. End Ave., New York, N.Y. 10023

[21] Appl. No.: 902,993

[22] Filed: Jun. 23, 1992

[51] Int. Cl.$^5$ .......................................... A61M 25/02
[52] U.S. Cl. .......................... 604/180; 128/DIG. 26
[58] Field of Search ............... 604/174, 177, 179, 180; 128/DIG. 26, DIG. 6; 602/54, 57

[56] References Cited

U.S. PATENT DOCUMENTS

| | | | |
|---|---|---|---|
| 2,712,312 | 7/1955 | Deker et al. | 602/57 |
| 3,834,380 | 9/1974 | Boyd | 128/DIG. 26 |
| 4,324,236 | 4/1982 | Gordon | 604/177 |
| 4,333,468 | 6/1982 | Geist | 604/180 |
| 4,413,621 | 11/1983 | McCracken et al. | 602/57 |
| 4,460,356 | 7/1984 | Moseley | 604/180 |
| 4,598,004 | 7/1986 | Heinecke | 602/57 |
| 4,614,183 | 9/1986 | McCracken et al. | 604/180 |
| 4,737,143 | 4/1988 | Russell | 604/180 |
| 4,807,613 | 2/1989 | Koehnke et al. | 602/57 |
| 4,822,342 | 4/1989 | Brawner | 604/180 |
| 4,917,929 | 4/1990 | Heinecke | 602/57 |
| 5,042,466 | 8/1991 | McKnight | 602/54 |
| 5,098,399 | 3/1992 | Tollini | 604/180 |

Primary Examiner—Paul J. Hirsch
Attorney, Agent, or Firm—R. Neil Sudol; Henry D. Coleman

[57] ABSTRACT

A device for use in securing an intravenous tube to a catheter comprises a tape strip and a releasable cover strip. The tape strip has, along one side, a central region provided with a layer of adhesive and two end regions on opposite sides of the central region, the end regions being adhesive free. The cover strip is attached to the layer of adhesive for temporarily protecting the layer of adhesive and preventing premature sticking thereof to a surface. In securing an intravenous tube to a catheter, the intravenous tube is first connected to the catheter to form a junction therebetween, and the tape strip is wrapped around both the intravenous tube and the catheter at the junction so that the tape strip is bonded to both the intravenous tube and the catheter via the layer of adhesive and so that the end regions of the tape strip are juxtaposed to one another.

3 Claims, 1 Drawing Sheet

TAPE STRIP AND ASSOCIATED METHOD OF CONNECTING TUBULAR MEMBERS

BACKGROUND OF THE INVENTION

This invention relates to a strip of adhesive type tape. This invention also relates to a method wherein the tape strip is used to temporarily secure two tubes to one another. This invention is particularly useful in hospitals and other health care institutions to bind an intravenous tube to an intravenous catheter.

Intravenous tubes are used for feeding all manner of intravenous fluid to patients in hospitals and other health care institutions. Frequently, the intravenous fluid is vital to continuance of a patient's life. Accordingly, it is crucial that the intravenous tube remains connected to the catheter.

It happens occasionally that an intravenous tube and/or its catheter is inadvertently withdrawn from the blood vessel to which the catheter is attached. Although a number of solutions have been proffered for obviating the accidental removal of intravenous catheters, no convenient technique is known for securing an intravenous tube to a catheter in an effective, simple way.

OBJECTS OF THE INVENTION

An object of the present invention is to provide a tape strip for attaching one tubular member to another.

Another object of the present invention is to provide such a tape strip which is easy to attach and subsequently easy to remove from a catheter and intravenous tube.

Another, more particular, object of the present invention is to provide such a tape strip which is easy and inexpensive to manufacture.

A further object of the present invention is to provide a method for releasably attaching one tubular member to another, particularly for removably securing an intravenous tube to an intravenous catheter.

Another particular object of the present invention is to provide such a method which is simple.

Other objects of the present invention will be apparent from the detailed descriptions and drawings included herein.

SUMMARY OF THE INVENTION

A device for use in securing two tubes to one another comprises, in accordance with the present invention, a tape strip and a releasable cover strip. The tape strip has, along one side, a central region provided with a layer of adhesive and two end regions on opposite sides of the central region, the end regions being adhesive free. The cover strip is attached to the layer of adhesive for temporarily protecting the layer of adhesive and preventing premature sticking thereof to a surface. Accordingly, the cover strip is at least coextensive with the layer of adhesive.

Pursuant to another feature of the present invention, the cover strip is one of two separate cover strips each provided with a respective pull tab. The cover strips each protect a portion of the adhesive layer and together are at least coextensive therewith. Preferably, the two cover strips are of similar size and are symmetrically disposed with respect to the tape strip.

According to another feature of the present invention, the layer of adhesive extends along the one side from one of the end regions to the other.

A method for securing an intravenous tube to an intravenous catheter comprises the steps of (a) connecting the intravenous tube to the catheter to form a junction therebetween, (b) providing a tape strip having, along one side, a central region provided with a layer of adhesive and two end regions on opposite sides of the central region, the end regions being adhesive free, and (c) wrapping the tape strip around both the intravenous tube and the catheter at the junction so that the tape strip is bonded to both the intravenous tube and the catheter via the layer of adhesive and so that the end regions of the tape strip are juxtaposed to one another.

Where the tape strip is provided with a releasable cover attached to the layer of adhesive for temporarily protecting the layer of adhesive and preventing premature sticking thereof to a surface, the method further comprises the step of removing the cover from the layer of adhesive prior to the wrapping of the tape strip around the intravenous tube and the catheter.

To remove the tape strip from the intravenous tube and the catheter, the end regions of the tape strip are grasped and pulled.

A tape strip in accordance with the present invention is easy to attach and subsequently easy to remove from a catheter and intravenous tube. Also, the tape strip is easy and inexpensive to manufacture.

DETAILED DESCRIPTION

Figure 1:
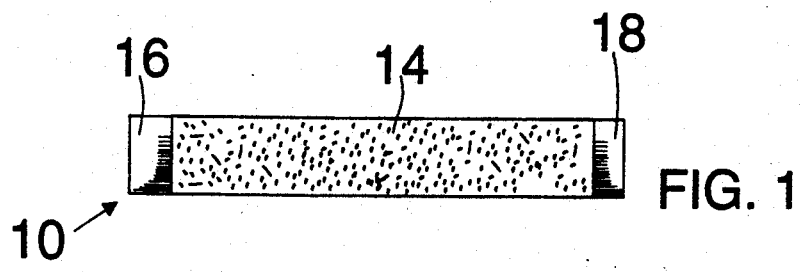
FIG. 1 is a plan view of a tape strip for use in a fastening technique in accordance with the present invention.
Figure 2:
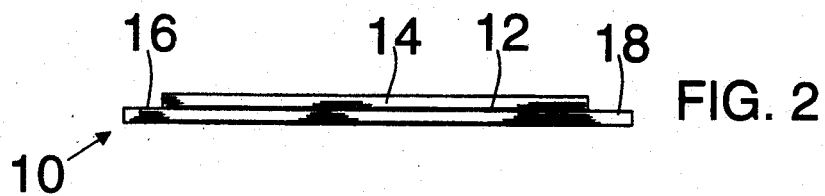
FIG. 2 is a side elevational view of the tape strip of FIG. 1.

As illustrated in FIGS. 1 and 2, a device for use in securing two tubes to one another comprises a tape strip 10 having, along one side 12, a central region provided with a layer of adhesive 14 and two end regions 16 and 18 on opposite sides of the central region. End regions 16 and 18 are adhesive free.

Figure 3:
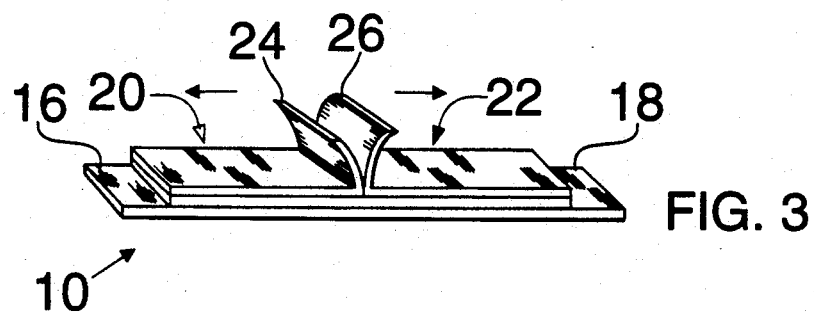
FIG. 3 is a perspective view of the tape strip of FIGS. 1 and 2, showing the tape strip provided with a pair of releasable cover strips.

As illustrated in FIG. 3, a pair of releasable cover strips 20 and 22 are attached to adhesive layer 14 for temporarily protecting the adhesive layer and preventing premature sticking thereof to a surface. Cover strips 20 and 22 are at least coextensive with adhesive layer 14. Cover strips 20 and 22 may extend beyond adhesive layer 14 to also cover end regions 16 and 18.

Cover strips 20 and 22 are respectively provided with pull tabs 24 and 26 which are grasped and pulled apart from one another to remove cover strips 20 and 22 from adhesive layer 14. Cover strips 20 and 22 each protect a half of adhesive layer 14. Thus, strips 20 and 22 are identical in size and shape and are symmetrically disposed with respect to tape strip 10.

Figure 4:
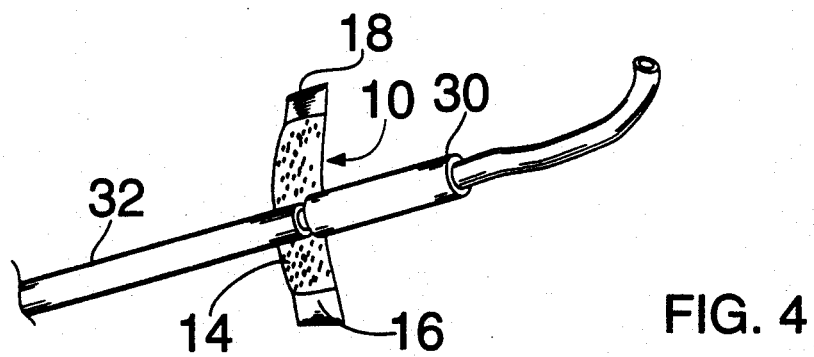
FIG. 4 is a perspective view showing an early step in the application of the tape strip of FIGS. 1-3 to an intravenous tube and catheter.
Figure 5:
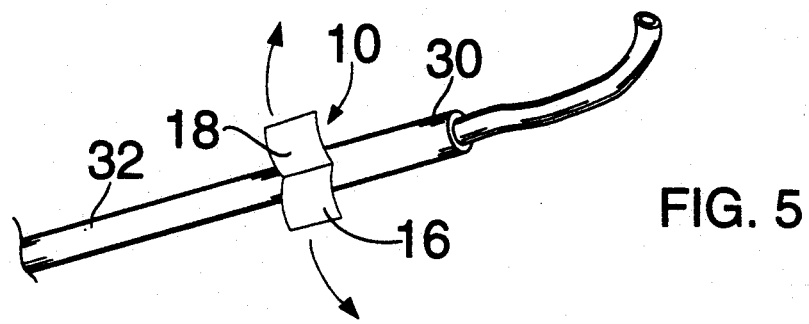
FIG. 5 is a perspective view similar to FIG. 4, showing the tape strip as fully applied to the intravenous tube and catheter.

As depicted in FIG. 4, an intravenous tube 30 connected to a catheter 32 to form a junction therebetween is secured to the catheter by tape strip 10. Adhesive layer 14 of tape strip 10 is brought into contact with tube 20 and catheter 32 along one side thereof, as shown in FIG. 4. Tape strip 10 is then wrapped around both intravenous tube 30 and catheter 32 at the junction therebewteen so that strip 10 is bonded to both intravenous tube 30 and catheter 32 via adhesive layer 14 and so that end regions 16 and 18 are juxtaposed to one another (FIG. 5). Thus, end regions 16 and 18 form pull tabs which are grasped and pulled apart from one another in order to remove adhesive layer 14 and concomitantly tape strip 10 from intravenous tube 20 and catheter 32.

In securing tape strip 10 to intravenous tube 30 and catheter 32, cover strips 20 and 22 are partially separated from adhesive layer 14 prior to a pressing of adhesive layer 14 to tube 30 and catheter 32 along one side thereof. In addition, strip 10 may be partially wound about tube 30 and catheter 32 prior to the complete removal of cover strips 20 and 22 from adhesive layer 14. This procedure ensures that the adhesiveness of and sterility of layer 14 are not compromised during application of tape strip 10.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for securing an intravenous tube to an intravenous catheter, comprising the steps of:

connecting the intravenous tube to the catheter to form a junction therebetween;

providing a tape strip having, along one side, a central region provided with a layer of adhesive and two end regions on opposite sides of said central region, said end regions being adhesive free; and wrapping said tape strip around both said intravenous tube and said catheter at said junction so that said tape strip is bonded to both said intravenous tube and said catheter via said layer of adhesive and so that said end regions are juxtaposed to one another.

2. The method defined in claim 1 wherein said tape strip is provided with releasable cover means attached to said layer of adhesive for temporarily protecting said layer of adhesive and preventing premature sticking thereof to a surface, said cover means being at least coextensive with said layer of adhesive, further comprising the step of removing said cover means from said layer of adhesive prior to said step of wrapping.

3. The method defined in claim 1, further comprising the step, executed upon completion of said step of wrapping, of grasping said end regions and pulling on said end regions to remove said tape strip from around said intravenous tube and said catheter.

* * * * *